(12) United States Patent
Fukunishi et al.

(10) Patent No.: US 8,486,919 B2
(45) Date of Patent: Jul. 16, 2013

(54) 4-ALKYLRESORCINOL DERIVATIVE AND EXTERNAL PREPARATION FOR SKIN CONTAINING THE SAME

(75) Inventors: Hirotada Fukunishi, Yokohama (JP); Rikako Suzuki, Yokohama (JP); Kiyoshi Sato, Yokohama (JP); Masaru Suetsugu, Yokohama (JP)

(73) Assignee: Shiseido Company, Ltd., Chuo-ku, Tokyo (JP)

( * ) Notice: Subject to any disclaimer, the term of this patent is extended or adjusted under 35 U.S.C. 154(b) by 0 days.

(21) Appl. No.: 13/809,696

(22) PCT Filed: Jun. 1, 2011

(86) PCT No.: PCT/JP2011/062575
§ 371 (c)(1),
(2), (4) Date: Jan. 11, 2013

(87) PCT Pub. No.: WO2012/008231
PCT Pub. Date: Jan. 19, 2012

(65) Prior Publication Data
US 2013/0109878 A1    May 2, 2013

(30) Foreign Application Priority Data

Jul. 16, 2010 (JP) ................................. 2010-161274

(51) Int. Cl.
*A61K 31/6615*   (2006.01)
*C07F 9/12*      (2006.01)

(52) U.S. Cl.
USPC ........................................... 514/107; 558/162

(58) Field of Classification Search
USPC ........................................... 558/162; 514/107
See application file for complete search history.

(56) References Cited

U.S. PATENT DOCUMENTS
6,132,740 A    10/2000    Hu

FOREIGN PATENT DOCUMENTS
JP    2004-10598    1/2004
JP    2005-179238   7/2005

OTHER PUBLICATIONS

Espacenet bibliographic data for JP 2004010598 published Jan. 15, 2004, one page.
Espacenet bibliographic data for JP 2005179238 published Jul. 7, 2005, one page.
International Search Report for corresponding PCT/JP2011/062575 mailed Aug. 30, 2011, four pages.
Welch et al., "Reduction of Aryl Diethyl Phosphates with Titanium Metal: A Method for Deoxygenation of Phenols," J. Org. Chem., vol. 43, No. 25, 1978, pp. 4797-4799.

*Primary Examiner* — Kristin Bianchi
(74) *Attorney, Agent, or Firm* — Rankin, Hill & Clark LLP

(57) ABSTRACT

The present invention provides a compound that has a high whitening effect and is excellent in safety and stability and provides an external preparation for skin comprising the same. The compound of the present invention is a 4-alkylresorcinol derivative represented by formula (1) or a salt thereof:

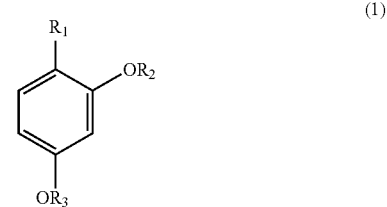

wherein $R_1$ is a branched or cyclic alkyl group of 3 to 7 carbon atoms or a linear alkyl group of 2 to 5 carbon atoms; $R_2$ and $R_3$ are each independently a hydrogen atom or a group represented by $-P(O)(OR_4)(OR_5)$, and at least one of $R_2$ and $R_3$ is a group represented by $-P(O)(OR_4)(OR_5)$; and $R_4$ and $R_5$ are each independently a hydrogen atom or a linear or branched alkyl group of 2 to 5 carbon atoms.

12 Claims, No Drawings

4-ALKYLRESORCINOL DERIVATIVE AND EXTERNAL PREPARATION FOR SKIN CONTAINING THE SAME

RELATED APPLICATIONS

This application claims the priority of Japanese Patent Application No. 2010-161274 filed on Jul. 16, 2010, which is incorporated herein by reference.

FIELD OF THE INVENTION

The present invention relates to a resorcinol derivative, and in particular, relates to a 4-alkylresorcinol derivative that has a high whitening effect and is excellent in safety and stability.

BACKGROUND ART

The pigment deposition such as pigmented spots and freckles on the skin is caused by the acceleration of melanin production, which is triggered by hormonal abnormality or ultraviolet stimulation, in the epidermal pigment cells and the excessive melanin deposition in the epidermis.

In order to prevent and improve such abnormal deposition of melanin pigment, a whitening agent is blended in external preparations for skin. Many of the whitening agents contain a compound having a melanin production inhibitory action as the active component.

Thus far, many studies have been carried out concerning the compounds having a whitening effect. For example, the in Patent Literatures 1 to 5, it is described that 4-alkylresorcinols have a whitening effect.

However, they have not been satisfactory in effect, safety, and stability.

PRIOR LITERATURES

Patent Literatures

Patent Literature 1: Japanese Unexamined Patent Publication No. H02-49715
Patent Literature 2: Japanese Unexamined Patent Publication No. 2002-540095
Patent Literature 3: Japanese Unexamined Patent Publication No. H11-152203
Patent Literature 4: Japanese Unexamined Patent Publication No. 2006-124357
Patent Literature 5: Japanese Unexamined Patent Publication No. 2006-124358

SUMMARY OF THE INVENTION

Problem to be Solved by the Invention

The present invention was made in view of the above-described background art, and an object is to provide a compound that has a high whitening effect and is excellent in safety and stability.

Means to Solve the Problem

The present inventors have diligently studied; as a result, the present inventors have found that specific 4-alkylresorcinol derivatives have an excellent melanin production inhibitory action and their safety and stability are also high, thus leading to the completion of the present invention.

That is, the 4-alkylresorcinol derivative according to the present invention is represented by formula (1) or a salt thereof:

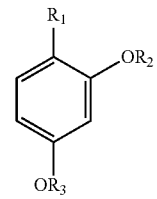

(1)

wherein $R_1$ is a branched or cyclic alkyl group of 3 to 7 carbon atoms or a linear alkyl group of 2 to 5 carbon atoms; $R_2$ and $R_3$ are each independently a hydrogen atom or a group represented by $-P(O)(OR_4)(OR_5)$, and at least one of $R_2$ and $R_3$ is a group represented by $-P(O)(OR_4)(OR_5)$; and $R_4$ and $R_5$ are each independently a hydrogen atom or a linear or branched alkyl group of 2 to 5 carbon atoms.

The present invention provides the 4-alkylresorcinol derivative or a salt thereof, wherein both $R_2$ and $R_3$ are groups represented by $-P(O)(OR_4)(OR_5)$.

The present invention also provides the 4-alkylresorcinol derivative or a salt thereof, wherein both $R_4$ and $R_5$ are hydrogen atoms.

The external preparation for skin according to the present invention is characterized by comprising one or more selected from any of the 4-alkylresorcinol derivatives and pharmacologically acceptable salts thereof.

The skin-whitening agent according to the present invention is characterized by comprising one or more selected from any of the 4-alkylresorcinol derivatives and pharmacologically acceptable salts thereof as active components.

Effect of the Invention

The 4-alkylresorcinol derivatives of the present invention have excellent melanin production inhibitory action and have no cytotoxicity. Thus, an external preparation for skin with a high whitening effect and safety can be obtained by blending the 4-alkylresorcinol derivative of the present invention. In addition, the 4-alkylresorcinol derivatives of the present invention are not discolored by light: thus, the stability is excellent.

MODES FOR CARRYING OUT THE INVENTION

The 4-alkylresorcinol derivative of the present invention is represented by the following formula (1).

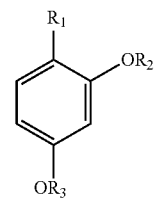

(1)

In formula (1), $R_1$ is a branched or cyclic alkyl group of 3 to 7 carbon atoms or a linear alkyl group of 2 to 5 carbon atoms.

Examples of branched alkyl groups of 3 to 7 carbon atoms include isopropyl, isobutyl, sec-butyl, tert-butyl, isopentyl, neopentyl, 1-methylbutyl, 1-ethylpropyl, 1-ethyl-2-methylpropyl, and 1-isopropyl-2-methylpropyl; however, they are not limited by these. The branching positions and the number of branches in the branched alkyl group are arbitrary and they are not limited in particular.

The cyclic alkyl group of 3 to 7 carbon atoms may contain at least one saturated hydrocarbon ring and the total number of carbon atoms of the saturated hydrocarbon group may be 3 to 7. Examples thereof include cyclopentyl, cyclohexyl, 4-methylcyclopentyl, 1,4-dimethylcyclopentyl, 2-cyclopentylethyl, 4-methylcyclohexyl, and cyclohexylmethyl.

Examples of linear alkyl groups of 2 to 5 carbon atoms include ethyl, propyl, butyl, and pentyl.

$R_2$ and $R_3$ are each independently a hydrogen atom or a group represented by $-P(O)(OR_4)(OR_5)$, and at least one of $R_2$ and $R_3$ is a group represented by $-P(O)(OR_4)(OR_5)$.

$R_4$ and $R_5$ are each independently a hydrogen atom or a linear or branched alkyl group of 2 to 5 carbon atoms.

Thus, the 4-alkylresorcinol derivative of the present invention is a phosphate ester of a 4-alkylresolcinol wherein the hydrogen atom of at least one of phenolic hydroxyl groups of the 4-alkylresorcinol is substituted with the group $-P(O)(OR_4)(OR_5)$.

As one of preferable examples of the 4-alkylresorcinol derivatives of the present invention, the one wherein both $R_2$ and $R_3$ are groups represented by $-P(O)(OR_4)(OR_5)$ can be listed.

As another one of preferable examples, the one wherein both $R_4$ and $R_5$ are hydrogen atom s can be listed.

The 4-alkylresorcinol derivative of the present invention can be synthesized by a publicly known method. Typically, it can be synthesized by carrying out a phosphorylation reaction of a 4-alkylresorcinol. For example, 4-alkylresorcinol is reacted with sodium hydride in a solvent such as THF and then further reacted with an alkyl halophosphate, thereby obtaining a 4-alkylresorcinol derivative wherein at least one of $R_2$ and $R_3$ is the group $-P(O)(OR_4)(OR_5)$ (and wherein $R_4$ and $R_5$ are as defined above, but at least one of them is an alkyl group) can be obtained (refer to J. Org. Chem. Vol. 43, No. 25, p. 4797-4799 (1978) etc.).

Alternatively, a 4-alkylresorcinol is phosphorylated by the use of a dibenzyl halophosphate etc. instead of the alkyl halophosphate and then the benzyl group is removed with catalytic reduction in the presence of Pd—C, thereby obtaining a 4-alkylresorcinol derivative wherein at least one of $R_2$ and $R_3$ is the group $-P(O)(OR_4)(OR_5)$ (and wherein $R_4$ and $R_5$ are hydrogen atoms) can be obtained.

In addition to them, the 4-alkylresorcinol derivative of the present invention can be obtained by a method wherein phosphoryl chloride is used (Biochimica et Biophysica Acta; vol. 13; (1954); p. 260, 267, and WO2008/103415) or a method wherein diphosphorus pentaoxide is used (Bulletin of the Chemical Society of Japan; vol. 80; nb. 7; (2007); p. 1429-1434), etc.

The 4-alkylresorcinols can be synthesized by the methods described in the above-described Patent Literatures 1 to 5 or other literatures.

As alkyl halophosphates and benzyl halophosphates, commercial products can be used; in addition, those synthesized by publicly known methods may be used. For example, they can be synthesized by reacting the corresponding alcohol and phosphorus oxychloride at 0 to 20° C. in a nonpolar solvent such as toluene, chlorobenzene or dichlorobenzene in the presence of a base such as trimethylamine, triethylamine, or N,N-dimethylaniline.

When $R_4$ and/or $R_5$ is a hydrogen atom, they can be converted, as necessary, to salts thereof by the ordinary method. Examples thereof include the salts of alkali metals or alkaline earth metals such as sodium, potassium, calcium, and magnesium and preferably, sodium salts and potassium salts.

The 4-alkylresorcinol derivative of the present invention has an excellent melanin production inhibitory effect, and the effect is higher than that of the corresponding 4-alkylresorcinol (i.e., $R_2=R_3=H$). In addition, the 4-alkylresorcinol derivative of the present invention has no cytotoxicity, and the safety is excellent; therefore, it is possible to blend a large amount thereof into external preparations for skin. Furthermore, the 4-alkylresorcinol derivative of the present invention is also very excellent in photostability.

Accordingly, the 4-alkylresorcinol derivative of the present invention is useful as a whitening agent, and it can be suitably blended into an external preparation for skin, in particular, into an external preparation for skin intended for the improvement and inhibition of pigmented spots, freckles, and skin dullness.

When the 4-alkylresorcinol derivative of the present invention is blended in an external preparation for skin, the blending quantity in the external preparation for skin, which is not limited in particular, is normally 0.01 mass % or higher, and preferably 0.1 mass % or higher. If the blending quantity is too small, the effect may not be satisfactorily achieved. The upper limit, which is not limited in particular, is normally 10 mass % or lower, preferably 5 mass % or lower, and more preferably 1 mass % or lower. Even when an excess amount is blended, the prominent improvement of the effect that is proportionate to the total amount may not be obtained.

The external preparation for skin of the present invention can be produced by an ordinary method except for the blending of the 4-alkylresorcinol derivative.

In the external preparation for skin of the present invention, in addition to the 4-alkylresorcinol derivative, so far as the effect of the present invention is not undermined, other components that are normally used in the external preparations for skin, such as cosmetics and pharmaceuticals, can be suitably blended as necessary; examples of such components include oil, wetting agents, UV protective agents, antioxidants, sequestering agents, surfactants, preservatives, moisturizers, perfumes, water, alcohols, thickeners, powder, coloring materials, crude drugs, and various other medicinal ingredients.

Also, other whitening agents such as vitamin C, magnesium ascorbyl phosphate, ascorbyl glucoside, arbutin, kojic acid, Rucinol, ellagic acid, tranexamic acid, and linoleic acid can be appropriately blended.

The external preparation for skin of the present invention is widely applicable in the fields of cosmetics, pharmaceuticals, and quasi-drugs. The form of skin preparation is not limited in particular so far as it is applicable to the skin. Examples thereof include solution, emulsion, solid, semi-solid, powder, powder dispersion, water-oil bilayer, water-oil-powder trilayer, ointment, gel, aerosol, mousse, stick, etc.; thus any form of skin preparation can be applied. Furthermore, its type of usage is arbitrary, and the examples include facial cosmetics such as lotion, milky lotion, cream, pack, essence, and gel; and makeup cosmetics such as foundation, pre-makeup, and concealer.

Hereinafter, the present invention will be further explained with reference to specific examples. However, the present invention is not limited by these examples.

EXAMPLES

Melanin Production Inhibition Test and Cytotoxicity Test

The melanin production inhibitory effect and the cytotoxicity was studied according to the following method.

(1) Inoculation of Cells and Addition of Test Substances

Mouse B16 melanoma cells were inoculated in a six well plate at 100,000 cells/well. The next day, test substance solutions (solvent: dimethylsulfoxide) were added thereto and then subjected to the melanin production inhibition test and cytotoxicity test.

(2) Cell Proliferation Test

Three days after the addition of the test substance solution, the medium was removed by aspiration. Then 1 mL of EMEM medium containing 10% Alamar Blue solution was added, and a reaction was allowed to proceed at 37° C. After 30 minutes, 100 μL of the reaction mixture was transferred to a 96 well plate and fluorescence was measured at an excitation wavelength of 544 nm and a measurement wavelength of 590 nm. Using the value thus measured as a relative value of cell count, a ratio of the cell count (% cell count) of the test substance-added group to the test substance-absent group (group in which only the solvent was added) was calculated. The higher the % cell count, the lower the cytotoxicity.

(3) Melanin Production Inhibition Test

Three days after the addition of the test substance solution, the medium was removed by aspiration. The cells were washed with a buffer (50 mM phosphate buffer, pH6.8), and then lysed by addition of 1M NaOH to measure an absorbance at 475 nm. Using the value thus measured as a relative value of the melanin amount, a ratio of the melanin amount (%) of the test substance-added group to the test substance-absent group (group in which only the solvent was added) was calculated. The lower the ratio of the melanin amount, the higher the melanin production-inhibitory effect.

Table 1 shows the results for the compounds of the present invention: 1,3-bisphosphonooxy-4-ethylbenzene (Compound 1), 1,3-bisphosphonooxy-4-isopropylbenzene (Compound 2), and 1,3-bisphosphonooxy-4-cyclohexylbenzene (Compound 3).

As seen from the melanin amount ratio, the compounds of the present invention have an excellent melanin production inhibitory effect, and there is no cytotoxicity even at high concentrations.

TABLE 1

| Test Compound* | Final Concentration of Test Compound (μM) | Melanin Amount Ratio (%) | Cell Count (%) |
|---|---|---|---|
| Compound 1 | 1.0 | 62 | 101 |
|  | 10 | 25 | 108 |
|  | 33 | 16 | 113 |
| Compound 2 | 1.0 | 47 | 99 |
|  | 9.6 | 16 | 95 |
|  | 32 | 13 | 103 |
|  | 0.9 | 48 | 102 |
| Compound 3 | 8.5 | 20 | 105 |
|  | 28 | 15 | 101 |

*Formula of each compound:

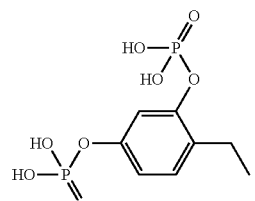

Compound 1

TABLE 1-continued

| Test Compound* | Final Concentration of Test Compound (μM) | Melanin Amount Ratio (%) | Cell Count (%) |
|---|---|---|---|

Compound 2

Compound 3

Table 2 shows the results for 4-ethylresoreinol (Comparative Compound 1), 4-isopropylresorcinol (Comparative Compound 2), and 4-cyclohexylresorcinol (Comparative Compound 3).

When Table 1 and Table 2 are compared, it can be seen that the compounds of the present invention display the melanin production inhibitory effect approximately similar to the comparative compounds at a lower concentration than the comparative compounds. That is, the compounds of the present invention can be said to have a higher melanin production inhibitory effect than the comparative compounds.

TABLE 2

| Test Compound* | Final Concentration of Test Compound (μM) | Melanin Amount Ratio (%) | Cell Count (%) |
|---|---|---|---|
| Comparative Compound 1 | 2.2 | 69 | 101 |
|  | 22 | 24 | 102 |
|  | 220 | 16 | 93 |
| Comparative Compound 2 | 2.0 | 32 | 99 |
|  | 6.6 | 17 | 97 |
|  | 66 | 12 | 98 |
| Comparative Compound 3 | 1.6 | 43 | 99 |
|  | 16 | 22 | 98 |
|  | 52 | 17 | 76 |

*Formula of each compound:

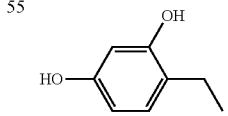

Comparative Compound 1

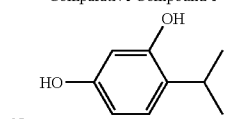

Comparative Compound 2

TABLE 2-continued

| Test Compound* | Final Concentration of Test Compound (μM) | Melanin Amount Ratio (%) | Cell Count (%) |
|---|---|---|---|

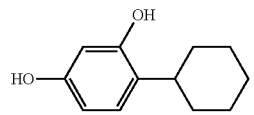

Comparative Compound 3

Test Example 2

Photostability Test

The solution of a test compound, which was placed into a transparent closed glass container, was subjected to sun exposure (50 MJ) or xenon (Xe) irradiation (for 96 hours), and then the appearance was observed with the naked eye. As a control, the container was covered with aluminum foil and completely light-shielded to be subjected to the sun exposure.

In Table 3 below, the results are shown for the compound of the present invention, 1,3-bisphosphonooxy-4-ethylbenzene (Compound 1) and 1,3-bis(diethylphosphonooxy)-4-ethylbenzene (Compound 4), and the comparative example, 4-ethylresorcinol (Comparative Compound 1). The solution concentrations of all the test compounds were 0.1 mass % (solvent: ethanol/water (20/80, v/v)).

As shown in Table 3, the coloration was observed, by light illumination, for the comparative compound. On the other hand, no appearance change was observed for the compounds of the present invention.

Thus, the 4-alkylresorcinol derivatives of the present invention are very excellent in photostability.

TABLE 3

| Test Compound | Control | Sun exposure | Xe irradiation |
|---|---|---|---|
| Compound 1 | colorless and transparent | colorless and transparent | colorless and transparent |
| Compound 4* | colorless and transparent | colorless and transparent | colorless and transparent |
| Comparative Compound 1 | colorless and transparent | yellow and transparent | orange and transparent |

*Compound 4:

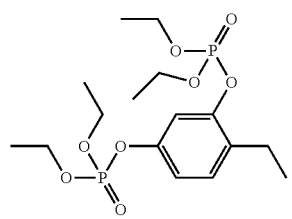 [SMILES: CCOP(=O)(OCC)Oc1ccc(CC)c(OP(=O)(OCC)OCC)c1]

Representative production examples of the 4-alkylresorcinol derivatives of the present invention are shown below. With the use of the corresponding raw materials, the desired 4-alkylresorcinol derivative can be obtained by carrying out a reaction according to these production examples.

Production Example 1

1,3-Bisphosphonooxy-4-ethylbenzene (Compound 1)

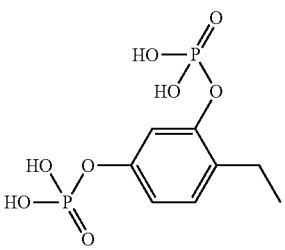 [SMILES: CCc1ccc(OP(=O)(O)O)cc1OP(=O)(O)O]

To a tetrahydrofuran solution (10 ml) of 4-ethylresorcinol (423 mg), sodium hydride (60% dispersion in liquid paraffin) (269 mg) was added and stirred at 0° C. for 30 minutes. Then, dibenzyl chlorophosphate (10 w/v % solution in benzene) (20 ml) was added dropwise. After stirring at room temperature for 3 hours, water (10 ml) was added to the reaction mixture, and the extraction was carried out with ethyl acetate (30 ml). Then, the extract was washed with saturated brine (10 ml), dried with anhydrous sodium sulfate and then concentrated. The residue (2.16 g) was subjected to silica gel chromatography (silica gel 60 g, chloroform to chloroform:methanol=50:1), to give 1,3-bis(dibenzylphosphonooxy)-4-ethylbenzene (1.65 g, yield: 84%) as a yellow liquid.

$^1$H-NMR (CDCl$_3$)δ: 1.13 (3H, t, J=7.7 Hz), 2.57 (2H, q, J=7.7 Hz), 5.09 (8H, m), 6.96 (1H, d, J=8.2 Hz), 7.08 (1H, d, J=8.2 Hz), 7.18 (1H, s), 7.32 (20H, m).

To an ethanol solution (10 ml) of 1,3-bis(dibenzylphosphonooxy)-4-ethylbenzene (1.09 g), 5% palladium-carbon (50% water-containing product) (97.3 mg) was added and stirred under a hydrogen atmosphere at room temperature for 7 hours. After the removal of the catalyst by filtration, the filtrate was concentrated, to give the title compound (463 mg, yield: 93%) as a pale yellow solid.

$^1$H-NMR (DMSO-d$_6$)δ: 1.12 (3H, t, J=7.7 Hz), 2.57 (2H, q, J=7.7 Hz), 5.5-6.7 (4H, brs), 6.90 (1H, d, J=8.2 Hz), 7.09 (1H, s), 7.16 (1H, d, J=8.2 Hz).

Production Example 2

1,3-Bisphosphonooxy-4-isopropylbenzene (Compound 2)

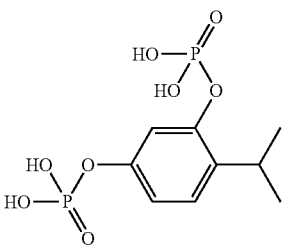 [SMILES: CC(C)c1ccc(OP(=O)(O)O)cc1OP(=O)(O)O]

To a tetrahydrofuran solution (10 ml) of 4-isopropylresorcinol (466 mg), sodium hydride (60% dispersion in liquid paraffin) (269 mg) was added and stirred at 0° C. for 30 minutes. Then, dibenzyl chlorophosphate (10 w/v % solution in benzene) (20 ml) was added dropwise. After stirring at room temperature for 3 hours, water (30 ml) was added to the reaction mixture, and the extraction was carried out with ethyl acetate (30 ml). Then, the extract was washed with saturated brine (20 ml), dried with anhydrous sodium sulfate and then concentrated. The residue (2.23 g) was subjected to silica gel chromatography (silica gel 76 g, chloroform to chloroform:methanol=70:1), to give 1,3-bis(dibenzylphosphonooxy)-4-isopropylbenzene (1.71 g, yield: 83%) as a yellow liquid.
$^1$H-NMR (CDCl$_3$) δ: 1.13 (6H, d, J=6.8 Hz), 3.19 (1H, septet, J=6.8 Hz), 5.04-5.13 (8H, m), 6.99 (1H, d, J=8.7 Hz), 7.14 (1H, d, J=8.7 Hz), 7.19 (1H, s), 7.30 (20H, m).

To an ethanol solution (10 ml) of 1,3-bis(dibenzylphosphonooxy)-4-isopropylbenzene (1.01 g), 5% palladium-carbon (50% water-containing product) (109 mg) was added and stirred under a hydrogen atmosphere at room temperature for 14 hours. After the removal of the catalyst by filtration, the filtrate was concentrated, to give the title compound (464 mg, yield: 100%) as a yellow paste.
$^1$H-NMR (DMSO-d$_6$) δ: 1.14 (6H, d, J=6.8 Hz), 3.25 (1H, septet, J=6.8 Hz), 4.5-6.2 (4H, brs), 6.93 (1H, d, J=8.2 Hz), 7.09 (1H, s), 7.21 (1H, d, J=8.2 Hz).

Production Example 3

1,3-Bisphosphonooxy-4-cyclohexylbenzene (Compound 3)

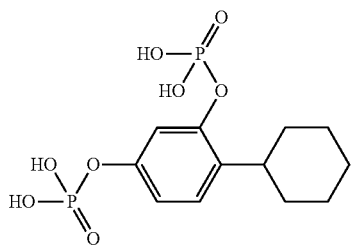 [SMILES: O=P(O)(O)Oc1ccc(C2CCCCC2)c(OP(=O)(O)O)c1]

To a tetrahydrofuran solution (10 ml) of 4-cyclohexylresorcinol (926 mg), sodium hydride (60% dispersion in liquid paraffin) (404 mg) was added and stirred at 0° C. for 30 minutes. Then, dibenzyl chlorophosphate (10 w/v % solution in benzene) (30 ml) was added dropwise. After stirring at room temperature for 3 hours, water (30 ml) was added to the reaction mixture, and the extraction was carried out with ethyl acetate (30 ml). Then, the extract was washed with saturated brine (20 ml), dried with anhydrous sodium sulfate and then concentrated. The residue (4.12 g) was subjected to silica gel chromatography (silica gel 90 g, chloroform to chloroform:methanol=100:1), to give 1,3-bis(dibenzylphosphonooxy)-4-cyclohexylbenzene (2.19 g, yield: 64%) as a yellow liquid.
$^1$H-NMR (CDCl$_3$) δ: 1.12-1.38 (5H, in), 1.66-1.82 (5H, m), 2.84 (1H, m), 5.09 (8H, in), 6.98 (1H, d, J=8.7 Hz), 7.13 (1H, d, J=8.7 Hz), 7.18 (1H, s), 7.30 (20H, m).

To an ethanol solution (10 ml) of 1,3-bis(dibenzylphosphonooxy)-4-cyclohexylbenzene (1.75 g), 5% palladium-carbon (50% water-containing product) (256 mg) was added and stirred under a hydrogen atmosphere at room temperature for 14 hours. After the removal of the catalyst by filtration, the filtrate was concentrated, to give the light yellow title compound (805 mg, yield: 93%).

$^1$H-NMR (DMSO-d$_6$) δ: 1.13-1.41 (5H, m), 1.60-1.85 (5H, in), 2.88 (1H, in), 6.7-8.2 (4H, brs), 6.92 (1H, d, J=8.2 Hz), 7.08 (1H, s), 7.18 (1H, d, J=8.2 Hz).

Production Example 4

1,3-Bis(diethylphosphonooxy)-4-ethylbenzene (Compound 4)

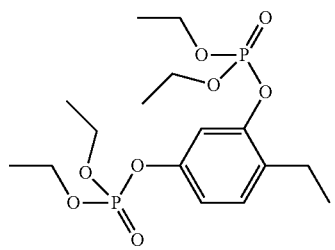 [SMILES: CCOP(=O)(OCC)Oc1ccc(CC)c(OP(=O)(OCC)OCC)c1]

To a tetrahydrofuran solution (10 ml) of 4-ethylresorcinol (691 mg), sodium hydride (60% dispersion in liquid paraffin) (440 mg) was added and stirred at 0° C. for 30 minutes. Then, diethyl chlorophosphate (1.73 ml) was added dropwise. After stirring at room temperature for 3 hours, water (10 ml) was added to the reaction mixture, and the extraction was carried out with ethyl acetate (30 ml). Then, the extract was washed with saturated brine (10 ml), dried with anhydrous sodium sulfate and then concentrated. The residue (2.43 g) was subjected to silica gel chromatography (silica gel 40 g, chloroform to chloroform:methanol=10:1), to give the title compound (2.05 g, yield: 100%) as a pale yellow oil.
$^1$H-NMR (CDCl$_3$)δ: 1.20 (3H, t, J=7.7 Hz), 1.36 (12H, m), 2.67 (2H, q, J=7.7m Hz), 4.22 (8H, m), 7.02 (1H, d, J=8.7 Hz), 7.16 (1H, d, J=8.7 Hz), 7.22 (1H, s).

Hereinbelow, formulation examples of the skin external preparation of the present invention are shown. Any of these exert a skin-whitening effect because of the addition of the 4-alkylresorcinol derivative of the present invention.

|  | mass % |
|---|---|
| Formulation Example 1 Skin lotion | |
| Trimethylglycine | 1.0 |
| Compound 1 | 0.5 |
| Glycerin | 1.0 |
| 1,3-Butylene glycol | 5.0 |
| Sodium alginate | 0.1 |
| Ethanol | 5.0 |
| Polyoxyethylene polyoxypropylene decyl tetradecyl ether | 0.2 |
| Sodium hexametaphosphate | q.s. |
| Citric acid | q.s. |
| Sodium citrate | q.s. |
| Phenoxyethanol | q.s. |
| Perfume | q.s. |
| Purified water | balance |
| Formulation Example 2 Skin lotion | |
| Compound 2 | 0.1 |
| Glycerin | 2.0 |
| 1,3-Butylene glycol | 4.0 |
| polyoxyethylene methylglucoside | 1.0 |
| PEG/PPG-14/7 dimethyl ether | 3.0 |
| Erythritol | 1.0 |
| Polyoxyethylene hydrogenated castor oil | 0.5 |
| Polyglyceryl diisostearate | 0.3 |
| Triethylhexanoin | 0.3 |
| Trisoditun EDTA | q.s. |

|  | mass % |
|---|---|
| Citric acid | q.s. |
| Sodium citrate | q.s. |
| Phenoxyethanol | q.s. |
| Purified water | balance |
| Formulation Example 3 Skin lotion | |
| Tranexamic acid | 1.0 |
| Potassium 4-methoxysalicylate | 1.0 |
| Lipoic acid | 0.1 |
| *Hamamelis* Leaf Extract | 0.1 |
| Hypotaurine | 0.1 |
| *Sophora flavescens* extract | 0.1 |
| Peach kernel extract | 0.1 |
| Beech sprout extract | 0.1 |
| Compound 3 | 1.0 |
| Magnesium ascorbyl phosphate | 0.1 |
| Thiotaurine | 0.1 |
| Green tea extract | 0.1 |
| Peppermint extract | 0.1 |
| Iris root extract | 1.0 |
| Trimethylglycine | 1.0 |
| Glycerin | 1.0 |
| 1,3-Butylene glycol | 5.0 |
| Hydroxyethylcellulose | 0.05 |
| Ethanol | 5.0 |
| Polyoxyethylene polyoxypropylene decyl tetradecyl ether | 0.2 |
| Trisodium EDTA | q.s. |
| Citric acid | q.s. |
| Sodium citrate | q.s. |
| Phenoxyethanol | q.s. |
| Perfume | q.s. |
| Purified water | balance |
| Formulation Example 5 Milky lotion | |
| Dipotassium glycyrrhizinate | 0.05 |
| Tocopheryl acetate | 0.5 |
| Compound 3 | 5.0 |
| Sodium L-glutamate | 0.05 |
| Fennel extract | 0.1 |
| Yeast extract | 0.1 |
| *Rehmannia* extract | 0.1 |
| Hydroxypropyl-β-cyclodextrin | 0.1 |
| Glycerin | 6.0 |
| 1,3-Butylene glycol | 5.0 |
| Polyoxyethylene methylglucoside | 3.0 |
| Sunflower oil | 1.0 |
| Squalane | 2.0 |
| Isododecane | 4.0 |
| Dimethylpolysiloxane | 3.0 |
| Xanthane gum | 0.1 |
| Carboxyvinyl polymer | 0.1 |
| Acrylic acid-alkyl methacrylate copolymer | 0.1 |
| Ethanol | 5.0 |
| Potassium hydroxide | q.s. |
| Sodium hexametaphosphate | q.s. |
| Red iron oxide | q.s. |
| Yellow iron oxide | q.s. |
| Ethylparaben | q.s. |
| Perfume | q.s. |
| Purified water | balance |
| Formulation Example 6 Milky lotion for daytime use | |
| Dipotassium glycyrrhizinate | 0.1 |
| Compound 2 | 0.05 |
| Tocopheryl acetate | 0.1 |
| 1,3-Butylene glycol | 5.0 |
| Squalane | 0.5 |
| Isododecane | 10.0 |
| Isohexadecane | 25.0 |
| Dimethylpolysiloxane | 2.0 |
| Polyoxyethlene-methylpolysiloxane copolymer | 1.5 |
| Tirmethylsiloxysilicate | 1.0 |
| 4-t-Butyl-4'-methoxydibenzoylmethane | 1.0 |
| 2-Ethylhexyl paramethoxycinnamate | 5.0 |
| Glyceryl mono-2-ethylhaxanoate diparamethoxycinnamate | 1.0 |
| Silicone-coated fine-particle titanium oxide | 4.0 |
| Dimethyldistearylammonium hectorite | 0.5 |
| Spherical polyethylene powder | 3.0 |
| Talc | 5.0 |
| Trisodium EDTA | q.s. |
| Phenoxyethanol | q.s. |
| Perfume | q.s. |
| Purified water | balance |
| Formulation Example 7 Milky lotion | |
| L-Arginine | 0.1 |
| Royal jelly extract | 0.1 |
| Yeast extract | 0.1 |
| Compound 1 | 10.0 |
| Stearyl glycyrrhetinate | 0.05 |
| Tocopheryl acetate | 0.1 |
| Acetylated sodium hyaluronate | 0.1 |
| Glycerin | 5.0 |
| Dipropylene glycol | 7.0 |
| Polyethylene glycol 1500 | 2.0 |
| Liquid paraffin | 7.0 |
| Petrolatum | 3.0 |
| Behenyl alcohol | 1.0 |
| Batyl alcohol | 2.0 |
| Jojoba oil | 1.0 |
| Stearic acid | 0.5 |
| Isostearic acid | 0.5 |
| Behenic acid | 0.5 |
| Pentaerythritol tetra-2-ethylhexanoate | 3.0 |
| Cetyl 2-ethylhexanoate | 3.0 |
| Glyceryl monostearate | 1.0 |
| Polyoxyethylene glyceryl monostearate | 1.0 |
| Carboxyvinyl polymer | 0.15 |
| Sodium hexametaphosphate | q.s. |
| Potassium hydroxide | q.s. |
| Methylparaben | q.s. |
| Perfume | q.s. |
| Purified water | balance |
| Formulation Example 8 Milky lotion | |
| Ascorbyl glucoside | 1.5 |
| Tranexamic acid | 1.0 |
| Tocopheryl acetate | 0.1 |
| Sodium hyaluronate | 0.05 |
| Compound 2 | 0.03 |
| Pantothenyl ethyl ether | 0.1 |
| Stearyl glycyrrhetinate | 0.1 |
| Glycerin | 7.0 |
| 1,3-Butylene glycol | 5.0 |
| Polyethylene glycol 20000 | 0.5 |
| Petrolatum | 2.0 |
| Jojoba oil | 3.0 |
| Squalane | 2.0 |
| Phytosteryl hydroxystearate | 0.5 |
| Behenyl alcohol | 0.5 |
| Batyl alcohol | 0.2 |
| Dimethylpolysiloxane | 2.0 |
| Pentaerythritol tetra-2-ethylhexanoate | 0.1 |
| Polyoxyethylene hydrogenated castor oil | 1.0 |
| Polyoxyethylene glyceryl isostearate | 3.0 |
| 4-t-Butyl-4'-methoxydibenzoylmethane | 0.1 |
| Glyceryl mono-2-ethylhaxanoate diparamethoxycinnamate | 0.1 |
| Xanthane gum | 0.1 |
| Carboxyvinyl polymer | 0.2 |
| Ethanol | 5.0 |
| Potassium hydroxide | q.s. |
| Sodium pyrosulfite | q.s. |
| Sodium hexametaphosphate | q.s. |
| Trisodium EDTA | q.s. |
| Yellow iron oxid | q.s. |
| Paraoxybenzoate | q.s. |
| Purified water | balance |
| Formulation Example 9 Cream | |
| Compound 3 | 0.05 |
| Potassium 4-methoxysalicylate | 3.0 |
| Propylene glycol | 5.0 |
| Glycerin | 8.0 |
| Stearic acid | 2.0 |
| Stearyl alcohol | 7.0 |
| Hydrogenated lanolin | 2.0 |

|  | mass % |
|---|---|
| Squalane | 5.0 |
| 2-Octyldodecyl alcohol | 6.0 |
| Polyoxyethylene cetyl ether | 3.0 |
| Glyceryl monostearate | 2.0 |
| Potassium hydroxide | q.s. |
| Ethylparaben | q.s. |
| Perfume | q.s. |
| Ion-exchange water | balance |
| Formulation Example 10 Cream | |
| Potassium 4-methoxysalicylate | 1.0 |
| 3-O-Ethyl ascorbic acid | 1.0 |
| Compound 1 | 0.3 |
| Coenzyme Q10 | 0.03 |
| Tranexamic acid | 2.0 |
| Tocopheryl acetate | 0.1 |
| Sodium hyaluronate | 0.05 |
| Pantothenyl ethyl ether | 0.1 |
| Stearyl glycyrrhetinate | 0.1 |
| Glycerin | 7.0 |
| 1,3-Butylene glycol | 5.0 |
| Polyethylene glycol 20000 | 0.5 |
| Petrolatum | 2.0 |
| Behenyl alcohol | 0.5 |
| Batyl alcohol | 0.2 |
| Squalane | 2.0 |
| Phytosteryl hydroxystearate | 0.5 |
| Jojoba oil | 3.0 |
| Pentaerythritol tetra-2-ethylhexanoate | 1.0 |
| Dimethylpolysiloxane | 2.0 |
| Polyoxyethylene glyceryl isostearate | 1.5 |
| Polyoxyethylene hydrogenated castor oil | 1.0 |
| Carboxyvinyl polymer | 0.2 |
| Xanthane gum | 0.1 |
| Ethanol | 5.0 |
| Sodium hexametaphosphate | q.s. |
| Yellow iron oxide | q.s. |
| Trisodium EDTA | q.s. |
| Potassium hydroxide | q.s. |
| Paraoxybenzoate | q.s. |
| Purified water | balance |
| Formulation Example 11 Two-layered milky lotion for daytime use | |
| Tranexamic acid | 2.0 |
| Potassium 4-methoxysalicylate | 1.0 |
| Compound 4 | 3.0 |
| Dipotassium glycyrrhizinate | 0.02 |
| Glutathione | 1.0 |
| Thiotaurine | 0.05 |
| Sophora angustifoilia root extract | 1.0 |
| Dipropylene glycol | 5.0 |
| Dimethylpolysiloxane | 5.0 |
| Isohexadecane | 25.0 |
| Polyoxyethlene-methylpolysiloxane copolymer | 2.0 |
| Dimethyldistearylammonium hectorite | 0.5 |
| Butyl ethyl propanediol | 0.5 |
| 2-Ethylhexyl paramethoxycinnamate | 7.5 |
| Tinnethylsiloxysilicate | 5.0 |
| Spherical alkyl polyacrylate powder | 5.0 |
| Dextrin palmitate-coated fine-particle zinc oxide | 15.0 |
| Trisodium EDTA | q.s. |
| Methylparaben | q.s. |
| Phenoxyethanol | q.s. |
| Perfume | q.s. |
| Purified water | balance |
| Formulation Example 12 Gel | |
| Potassium 4-methoxysalicylate | 0.1 |
| Lamium album extract | 0.1 |
| Compound 2 | 0.01 |
| Dipotassium glycyrrhizinate | 0.1 |
| Ascorbyl glucoside | 2.0 |
| Tocopheryl acetate | 0.1 |
| Scutellaria Baicalensis root extract | 0.1 |
| Saxifraga stolonifera extract | 0.1 |
| Glycerin | 2.0 |
| 1,3-Butylene glycol | 5.0 |

|  | mass % |
|---|---|
| Polyethylene glycol 1500 | 3.0 |
| Polyethylene glycol 20000 | 3.0 |
| Agar powder | 1.5 |
| Xanthane gum | 0.3 |
| Acrylic acid-alkyl methacrylate copolymer | 0.05 |
| Cetyl octanoate | 3.0 |
| Dimethylpolysiloxane | 5.0 |
| Sodium hexametaphosphate | q.s. |
| Dibutylhydroxytoluene | q.s. |
| Yellow iron oxide | q.s. |
| Citric acid | q.s. |
| Sodium citrate | q.s. |
| Sodium hydroxide | q.s. |
| Phenoxyethanol | q.s. |
| Perfume | q.s. |
| Purified water | balance |

What is claimed is:

1. A 4-alkylresorcinol derivative represented by formula (1) or a salt thereof:

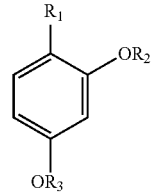

(1)

wherein $R_1$ is a branched or cyclic alkyl group of 3 to 7 carbon atoms or a linear alkyl group of 2 to 5 carbon atoms;

$R_2$ and $R_3$ are each independently a hydrogen atom or a group represented by $—P(O)(OR_4)(OR_5)$, and at least one of $R_2$ and $R_3$ is a group represented by $—P(O)(OR_4)(OR_5)$; and $R_4$ and $R_5$ are each independently a hydrogen atom or a linear or branched alkyl group of 2 to 5 carbon atoms.

2. The 4-alkylresorcinol derivative or a salt thereof according to claim 1, wherein both $R_2$ and $R_3$ are groups represented by $—P(O)(OR_4)(OR_5)$.

3. The 4-alkylresorcinol derivative or a salt thereof according to claim 1, wherein both $R_4$ and $R_5$ are hydrogen atoms.

4. An external preparation for skin comprising one or more selected from the 4-alkylresorcinol derivatives according to claim 1 and pharmacologically acceptable salts thereof.

5. A skin-whitening agent, wherein one or more selected from the 4-alkylresorcinol derivatives according to claim 1 and pharmacologically acceptable salts thereof are active components.

6. The 4-alkylresorcinol derivative or a salt thereof according to claim 2, wherein both $R_4$ and $R_5$ are hydrogen atoms.

7. An external preparation for skin comprising one or more selected from the 4-alkylresorcinol derivatives according to claim 6 and pharmacologically acceptable salts thereof.

8. A skin-whitening agent, wherein one or more selected from the 4-alkylresorcinol derivatives according to claim 6 and pharmacologically acceptable salts thereof are active components.

9. An external preparation for skin comprising one or more selected from the 4-alkylresorcinol derivatives according to claim 2 and pharmacologically acceptable salts thereof.

10. A skin-whitening agent, wherein one or more selected from the 4-alkylresorcinol derivatives according to claim 2 and pharmacologically acceptable salts thereof are active components.

11. An external preparation for skin comprising one or more selected from the 4-alkylresorcinol derivatives according to claim 3 and pharmacologically acceptable salts thereof.

12. A skin-whitening agent, wherein one or more selected from the 4-alkylresorcinol derivatives according to claim 3 and pharmacologically acceptable salts thereof are active components.

* * * * *